United States Patent [19]
DeLuca et al.

[11] Patent Number: 5,614,512
[45] Date of Patent: Mar. 25, 1997

[54] 20-OXO-PREGNACALCIFEROL ANALOGS WITH BINDING AFFINITY TO THE PROGESTERONE RECEPTOR

[75] Inventors: Hector F. DeLuca, Deerfield; Kato L. Perlman, Madison, both of Wis.; Rafal R. Sicinski, Warsaw, Poland; Hisham M. Darwish, Madison, Wis.

[73] Assignee: Wisconsin Alumni Research Foundation, Madison, Wis.

[21] Appl. No.: 539,343

[22] Filed: Oct. 5, 1995

[51] Int. Cl.$^6$ .............................. A61K 31/59; C07C 3/00
[52] U.S. Cl. ........................................... 514/167; 552/653
[58] Field of Search .................... 514/167; 552/653

[56] References Cited

U.S. PATENT DOCUMENTS 5,397,776  3/1995  DeLuca et al. ............... 514/167

Primary Examiner—Theodore J. Criares
Attorney, Agent, or Firm—Andrus, Sceales, Starke & Sawall

[57] ABSTRACT

A birth control method for a female mammal which comprises administering to the mammal an amount of a vitamin D compound sufficient to block binding of progesterone to the progesterone receptor in said mammal. The vitamin D compounds are 20-oxo-pregnacalciferol analogs, preferably 3-desoxy-20-oxo-19-nor-pregnacalciferol and its 2-oxo analog.

24 Claims, No Drawings

20-OXO-PREGNACALCIFEROL ANALOGS WITH BINDING AFFINITY TO THE PROGESTERONE RECEPTOR

This invention relates to biologically active vitamin D analogues useful as antagonists of progesterone suggesting a potential use for birth control.

BACKGROUND AND SUMMARY OF THE INVENTION

The 1α-hydroxylated metabolites of vitamin D—most importantly 1α,25-dihydroxyvitamin $D_3$ and 1α,25-dihydroxyvitamin $D_2$—are known as highly potent regulators of calcium homeostasis in animals and humans, and more recently their activity in cellular differentiation has also been established. V. Ostrem et al, Proc. Natl. Acad. Sci. U.S.A., (1987), 84, 2610. As a consequence, many structural analogues of these metabolites, such as compounds with different side chain structures, different hydroxylation patterns, or different stereochemistry, have been prepared and tested. Important examples of such analogues are 1α-hydroxyvitamin $D_3$, 1α-hydroxyvitamin $D_2$, various side chain fluorinated derivatives of 1α,25-dihydroxyvitamin $D_3$, and side chain homologated analogues. Several of these known compounds exhibit highly potent activity in vivo or in vitro, and some of these have been found to exhibit an interesting separation of activities in cell differentiation and calcium regulation. This difference in activity provides these compounds with advantageous therapeutic activity profiles and thus numerous of these compounds are in use, or have been proposed for use, in the treatment of a variety of diseases such as renal osteodystrophy, vitamin D-resistant rickets, osteoporosis, psoriasis, and certain malignancies.

Recently, a new class of vitamin D analogues has been discovered, i.e. the so-called 19-nor-vitamin D compounds. 19-nor-vitamin D compounds are vitamin D analogues in which the ring A exocyclic methylene group (carbon 19) typical of all vitamin D compounds has been removed and replaced by two hydrogen atoms. Specifically, these compounds exhibit a selective activity profile with high potency in inducing cellular differentiation, and minimal bone calcification activity. Such a differential activity profile renders these compounds useful for the treatment of malignancies, or the treatment of various skin disorders. Two different methods of synthesis of these 19-nor-vitamin D analogues have been described (Perlman et al, Tetrahedron Letters 31, 1823 (1990); Perlman et al, Tetrahedron Letters 32, 7663 (1991), and DeLuca et al, U.S. Pat. No. 5,086,191).

In Teutsch et al, U.S. Pat. No. 4,386,085, a 19-nor-steriod (referred to as RU 486) having strong antiprogesterone and antiglucocorticosteriod activities is described. When used in conjunction with synthetic prostaglandins RU 486 terminates pregnancy, which accounts for its wide interest. In addition it has potential as an antiglucocorticoid, and anti-estrogen agent.

Many analogues of RU 486 have been prepared, Etienne-Emile Baulieu: Science (1989) 245, 1351–1357, Chem. Eng. News (1991) 69 7–14, Schering's ZK 98299 (Federation Meeting 1992) 2037, all of which share with RU 486 the intact steroid A ring of progesterone with the conjugated 3-oxo-4-ene moiety. This feature is assumed to be responsible for binding to the progesterone receptor (PR).

In U.S. Pat. No. 5,397,776 vitamin D analogues with a progesterone side chain, but with the 3β-hydroxycyclohexane A-ring and double bond system characteristic of vitamin D were synthesized. The compounds prepared were 20-oxo-pregnacalciferol, 1α-hydroxy-20-oxopregnacaliciferol and 19-nor-1α-hydroxy-20-oxopregnacalciferol. All three compounds were examined for binding to the PR. Of the three 20-oxo analogues, only 20-oxo-pregnacalciferol did bind to the PR, indicating that the 1α-hydroxy group in the other two vitamin D-progesterone analogues prevents binding to the PR, and the absence of the 10–19 double bond in the 19-nor compound did not make a difference. None of the above three compounds had any calcemic activity nor did they bind to the vitamin D receptor.

It has been suggested, Teutsch et al, U.S. Pat. No. 4,386,085 May 31, 1983, Etienne-Emile Baulieu: Science (1989) 245, 1351–1357, that the A ring of RU 486 is necessary for binding to the PR. The ability of 20-oxo-pregnacalciferol to bind to the PR suggests that the progesterone A ring may not play as significant a role as had been assumed. Thus, as disclosed in U.S. Pat. No. 5,397,776, 20-oxo-pregnacalciferol is useful as an antagonist of progesterone, and thus blocks progesterone from binding to the PR. Since progesterone binding is necessary to maintain pregnancy, an abortion results. Compounds that block progesterone from binding to the PR, thus have potential for use in birth control either to prevent pregnancy or to abort pregnancy.

In an ongoing effort to examine the structural features responsible for binding properties to the PR, 20-oxo-pregnacalciferol analogs with 19-nor-3-desoxy-A rings were synthesized in which the exocyclic methylene group (carbon 19) and the 3-hydroxy group of the vitamin D molecule have been replaced by hydrogen atoms. The compounds prepared were 3-desoxy-20-oxo-19-nor-pregnacalciferol and 3-desoxy-2,20-dioxo-19-nor-pregnacalciferol and their binding to the PR was examined. The 3-desoxy-20-oxo-19-nor-pregnacalciferol did bind to the PR, but to a significantly lesser degree (40%) than the previously synthesized 20-oxo-pregnacalciferol. Interestingly, the intermediate 22-alcohol and the 22-aldehyde did also bind to the PR, the latter compound binding 1.5 times more than the 20-ketone. The biological results indicate, that an oxygen function in the A ring could be essential for improved binding to the PR. Attention was then turned to the 19-nor-pregnacalciferol analog with an oxo group in the A ring. It was found that 3-desoxy-2,20-dioxo-19-nor-pregnacalciferol has almost the same binding activity to the PR as the previously examined 20-oxo-pregnacalciferol, whereas the intermediate 22-alcohol, and the 22-aldehyde and the mono-protected 2,20-dione did also bind to the PR but to a lesser degree.

DISCLOSURE OF THE INVENTION

The present invention discloses a new series of 19-nor-vitamin D compounds, and further discloses a birth control method for a female mammal which comprises administering to the mammal an amount of vitamin D compound sufficient to prevent a pregnancy from occurring or if during pregnancy to cause an abortion in the mammal. Preferably, the vitamin D compound is administered in an amount of from about 0.1 mg/kg to about 20 mg/kg per day depending upon the vitamin D compound administered. Also, the vitamin D compound is preferably administered daily to the mammal for about 3 days to about 1 month.

As used herein the term "vitamin D compound" encompasses compounds which have the C-ring, D-ring and 3-desoxy-19-nor-cyclohexane A-ring of vitamin D interconnected by the 5, 7 diene double bond system of vitamin D together with a progesterone (—$COCH_3$), aldehyde (—COH) or alcohol (—OH) side chain attached to the D-ring.

Structurally, the new vitamin D compounds encompassed may be represented by the formula

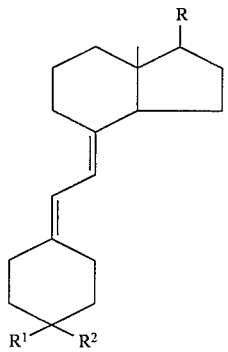

where $R^1$ and $R^2$ each represent hydrogen, or taken together $R^1$ and $R^2$ represent an oxo group or a ketal group of the type —O—$(CH_2)_n$—O— where n is an integer from 2 to 5, preferably 2, and the side chain group R in the above-shown structure, represents a progesterone side chain, i.e. —COCH$_3$, a 22-aldehyde side chain i.e. —CHCH$_3$CHO, or a 22-alcohol side chain i.e. —CHCH$_3$CH$_2$OH.

Some specific examples of such compounds include vitamin D metabolites or analogues such as 3-desoxy-20-oxo-19-nor-pregnacalciferol, 3-desoxy-22-hydroxy-19-nor-homopregnacalciferol, and 3-desoxy-22-aldehyde-19-nor-homopregnacalciferol. Others include 3-desoxy-2,20-dioxo-19-nor-pregnacalciferol, 3-desoxy-2-ethylene ketal-22-hydroxy-19-nor-homopregnacalciferol, 3-desoxy-2-ethylene ketal-22-aldehyde-19-nor-homopregnacalciferol, and 3-desoxy-2-ethylene ketal-20-oxo-19-nor-pregnacalciferol.

As used in the description and claims, "alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl," "fluoralkl" and "arylalkyl" refer to such an alkyl radical substituted by one or more hydroxy, fluoro or aryl groups respectively. An "acyl" group is an alkanoyl group of 1 to 6 carbons in all its isomeric forms, or an aroyl group, such as benzoyl, or halo-, nitro- or alkyl- substituted benzoyl groups, or an alkoxycarbonyl group of the type alkyl-O—CO—, such as methoxycarbonyl, ethoxycarbonyl, propyloxycarbonyl, etc., or a dicarboxylic acyl group such as oxalyl, malonyl, succinoyl, glutaroyl, or adipoyl. The term "aryl" signifies a phenyl-, or an alkyl-, nitro- or halo-substituted phenyl group. The term alkoxy signifies the group alkyl-O—.

This invention is more specifically described by the following illustrative examples. In these examples specific products identified by Arabic numerals (e.g. 1, 2, 3, etc.) refer to the specific structures so identified in the preceding description and in the Scheme.

EXAMPLE 1

Synthesis

For the synthesis of 3-desoxy-20-oxo-19-nor-pregnacalciferol (6a) we used our convergent approach, based on Lythgoe's concept and successfully applied by us to other 19-nor-vitamin D compounds. (Perlman, K. L.; DeLuca, H. F. *Tetrahedron Lett.* 1992, 33, 2937.) Thus, 22-acetoxy Grundmann's ketone analog 1 (Lythgoe, B.; Moran, T. A.; Nambudiry, M. E. N.; Ruston, S. J. *Chem. Soc. Perkin. Trans. I.* 1976, 2386.) was reacted with the conjugate (cyclohexylidene) ethyl diphenylphosphinoxy carbanion derived from 2a to give the expected diene 3a (n-BuLi, THF, −78° C., 1 h then 0° C., 18 h; 57%). Reduction of 22-ester 3a gave 22-alcohol 4a (LiAlH$_4$, THF, 0° C., 30 min then 20° C., 30 min) followed by Swern oxidation to give 22-aldehyde 5a ((COCl)$_2$, CH$_2$Cl$_2$, DMSO, −60° C., 30 min then TEA; overall 44%). The next step of the synthesis was Van Rheenen's (Van Rheenen, R. *Tetrahedron Lett.* 1969, 985.) unusual oxygenation procedure which we previously applied to the air sensitive pregnacalciferol system. (Perlman, K. L.; Hisham, D.; DeLuca, H. F. *Tetrahedron Lett.* 1994, 35, 2295.) Aldehyde intendedlate 5a was converted to the 20-keto derivative 6a in the presence of cupric acetate, complexed with 2,2'-bipyridyl or 1,10-phenanthroline as catalyst, the base 1,4-diazabicyclo[2.2.2]octane (Dabco) and DMF as solvent and air bubbled in the solution for 18 h (60%).

Experimental

All NMR in CDCl$_3$ at 500 MHz, All MS, EI, 70 ev.

19-Nor-3-desoxy-22-acetoxy-homopregnacalciferol (3a)

Phosphine oxide 1 (31.4 mg, 100 μmol) was dissolved in anhydrous THF (1 mL), cooled to 0° C. and n-BuLi (1.5M in hexanes, 75 μL, 108 μmol) added under argon with stirring. The solution turned deep orange. The mixture was cooled to −78° C. and the 22-acetoxy-Grundmann ketone 2a (27.1 μg, 108 μmol) added in anhydrous THF (200 μL+200 μL). The mixture was stirred under argon at −78° C. for 1 h (at that time the solution became colorless) and at rt for 18 h. Ethyl acetate was added and the organic phase washed with water, brine, dried (anh, MgSO$_4$), filtered and evaporated. The residue was dissolved in 20% ethyl acetate in hexane, passed through a silica Sep-Pak and washed with 40 mL of the same to give the 19-nor-homopregnacalciferol derivative 3a. The Sep-Pak was then washed with 20% 2-propanol in hexane to recover some unchanged diphenylphosphine oxide. Compound 3a was purified by HPLC (10% ethyl acetate in hexane, Zorbax Sil 9.4×25 cm) to give the 19-nor-homopregnacalciferol derivative 3a (2.5 mg, 57%).

3a. $^1$H NMR δ: 0.580 (3H, s, 18-CH$_3$), 1.025 (3H, d, J=6.8 Hz, 21-CH$_3$) 2.06 (3H, s, OCH$_3$), 2.83 (1H, m, 9β-H), 3.80 (1H, dd, J=10.7, 7.7 Hz, one of 22-H), 4.09 (1H, dd, J=10.7, 3.0 Hz, one of 22-H), 5.85 (1H, d, J=11.2 Hz, 7-H), 6.06 (1H, d, J-11.2 Hz, 6-H). MS m/z (rel. int.), 344 (M+, 100), 284 (62), 243 (38), 148 (48), 91 (60), 43 (55). UV (in EtOH) $\lambda_{max}$: 243, 251.5, 261 nm 19-Nor-3-desoxy-22-hydroxy-homopregnacalciferol (4a).

Acetoxy-homopregnacalciferol 3a (17 mg, 50 μmol), was dissolved in 1 mL anh THF cooled to 0° C. and LiAlH$_4$ (20 mg) added under argon with stirring. The mixture was stirred for an additional 30 min. at 0° C. and 25 min at RT. The mixture was cooled to 0° C. and the excess LiAlH$_4$ decomposed by the careful addition of wet ethyl acetate. More ethyl acetate was added, and the organic phase washed with water and brine, dried (anh. MgSO$_4$), filtered and evaporated. The residue was dissolved in 20% ethyl acetate in hexane, passed through a silica Sep-Pak and washed with the same to give the 19-nor-22-hydroxyhomopregnacalciferol derivative 4a (12 mg, 87%).

4a $^1$H NMR δ: 0.582 (3H, s, 18-CH$_3$), 1.062 (3H, d, J=6.7 Hz, 21-CH$_3$), 2.83 (1H, m, 9β-H), 3.39 (1H, m, one of 22-H), 3.65 (1H, m, one of 22-H), 5.85 (1H, d, J=11.1 Hz, 7-H),6.06 (1H, d, J-11.1 Hz, 6-H), UV (in EtOH) $\lambda_{max}$: 243, 251.5, 261 nm.

19-Nor-3-desoxy-homopregnacalciferol 22-aldehyde (5a).

A solution of oxalyl chloride (20 μL, 0.22 mmol) in anhydrous dichloromethane (0.5 mL) was added dropwise to a stirred solution of dimethyl sulfoxide (30 μL, 0.4 mmol) in 200 μL anhydrous dichloromethane at −60° C. under argon atmosphere. After the mixture was stirred for 10 min at −60° C., the solution of the alcohol 4a (11 mg, 36 μmol) in 500 μL anh dichloromethane was slowly added, and the flask was rinsed with an additional 200 μL anh dichloromethane. The mixture was stirred for 30 min at −60° C., and 500 μL triethylamine was added at −60° C. The mixture was stirred for 5 min, warmed to 0° C. and extracted with ether. The ether phase was washed with brine and dried (anh. $MgSO_4$), filtered and evaporated. The residue was dissolved in 30% ethyl acetate in hexane, passed through a silica Sep-Pak and washed with the same. The crude compound was purified by HPLC (10% ethyl acetate in hexane, Zorbax Sil 9.4×25 cm) to give the 19-nor-homopregnacalciferol-22-aldehyde derivative 5a (5.6 mg)

5a. $^1$H NMR δ: 0.606 (3H, s, 18-$CH_3$), 1.138 (3H, d, J=6.6 Hz, 21-$CH_3$), 2.84 (1H, μ, 9β-H), 5.86 (1H, d, J=11.2 Hz, 7-H) 6.06 (1H, d, J=11.2 Hz, 6-H), 9.59 (1H, d, J=3.0 Hz, 22-H). MS m/z (rel. int), 300 (M+ 25), 285 (13), 149 (43), 129 (28), 105 (42), 91 (75), 55 (100). UV (in EtOH) $\lambda_{max}$: 243, 251.5, 261 nm 19-Nor-3-desoxy-20-oxopregnacalciferol (6a).

A $CuAc_2$-dipyridyl-DABCO (1,4-diazabicyclo(2.2.2)octane) solution in anh DMF was prepared from dipyridyl (12 mg, 0.77 mmol) $CuAc_2$ (13 mg, 0.72 mmol) and DABCO (190 mg, 1.7 mmol) in anhydrous dimethyl formamide (2 mL). The 22-aldehyde 5a (2.8 mg, 10 μmol) was dissolved in anh. dimethyl formamide (0.5 mL) and the above $CuAc_2$-dipyridyl-DABCO DMF solution added (0.4 mL). The mixture was protected from light and air was bubbled into this solution for 22 h at RT with stirring. Water was added and the mixture extracted with ether. The ether phase was washed with brine and dried (anh. $MgSO_4$), filtered and evaporated. The residue was dissolved in 30% ethyl acetate in hexane, passed through a silica Sep-Pak and washed with the same. The crude compound was purified by HPLC (10% ethyl acetate in hexane, Zorbax Sil 9.4×25 cm) to give the 19-nor-20-oxopregnacalciferol derivative 6a (1.4 mg)

6a. $^1$H NMR δ: 0.514 (3H, s, 18-$CH_3$), 2.13 (3H, s, 21-$CH_3$), 2.85 (1H, m, 9β-H), 5.87 (1H, d, J=11.3 Hz, 7-H), 6.04 (1H, d, J=11.3 Hz, 6-H). MS m/z (rel. int), 286 (M+,65), 243 (55), 147 (75), 77 (55), 55 (45), 43 (100). exact mass calcd for $C_{20}H_{30}O$ 286.2297, found 286.2297. UV (in EtOH) $\lambda_{max}$: 243, 251.5, 261 nm.

EXAMPLE 2

Synthesis

For the synthesis of the 3-desoxy-2,20-dioxo-19-norpregnacalciferol (6c) we used the synthetic methodology described for 6a. We chose as our starting material commercially available 1,4-cyclohexanedione mono-ethylene ketal (7) as a ring-A building block. Peterson reaction with methyl (trimethylsilyl)acetate in the presence of LDA in THF gave the 4'-ethylenedioxycyclohexylidene ester 8 (−78° C., 2 h; 97%), which was subsequently reduced to the allylic alcohol 9 (DIBAL-H in toluene at −78° C., 72%). The alcohol 9 was transformed to the desired ring-A phosphine oxide 2b by in situ tosylation, conversion into the corresponding phosphine, followed by oxidation with hydrogen peroxide (TsCl, n-BuLi, 0° C. then $Ph_2PH$, n-BuLi, 0° C., 30 min then $H_2O_2$, $CHCl_3$, 0° C., 1 h; 77% overall yield). Wittig-Horner coupling of the CD ring ketone 1 with the anion of 2b gave pregnacalciferol analog 3b (n-BuLi, THF, −78° C., 1 h then 0° C., 18 h; 28%). Reduction of 3b gave quantitatively the alcohol 4b ($LiAlH_4$, THF, 0° C., 30 min then 20° C., 30 min) which underwent Swern oxidation to the aldehyde 5b (($COCl)_2$, $CH_2Cl_2$, DMSO, −60° C., 30 min then TEA; 68%). Van Rheenen's (Van Rheenen, R. Tetrahedron Lett. 1969, 985.) air oxygenation of 5b resulted in the formation of 20-keto compound 6b (60%). Careful removal of the ethylenedioxy group in the latter was done under controlled conditions with acetic acid-water (4:1) at 70° C. for 15 min, followed by immediate removal of the acetic acid by purging with nitrogen or azeotropic distillation with toluene. HPLC purification gave 2,20-dioxopregnacalciferol analog 6c (70%).

Experimental

4-Monoethylene ketal-cyclohexylidene acetic Acid Methyl Esters (8).

n-BuLi (18.8 mL, 1.6M in hexanes, 30mmol) was added to a solution of diisopropylamine (4.0 mL, 30 mmol) in anhydrous THF (20 mL) under argon at −78° C. with stirring and methyl (trimethylsilyl) acetate (4.9 mL, 30 mmol) was then added. After 15 min 1,4-cyclohexanedione mono-ethylene ketal (2.19 g, 14 mmol) in anhydrous THF (20+10 mL) was added. The solution was stirred for 2 h at −78° C. The reaction mixture was quenched with saturated ammonium chloride solution and extracted with ether. The combined ether fractions were washed with brine, water and dried (anh. $MgSO_4$), filtered and evaporated. The product was further purified by flash chromatography (5% ethyl acetate in hexane) to give (2.9 g, 97%) of 8. $^1$H NMR ($CDCl_3$, 500 MHz) δ1.771 (4H, m), 2.38 (2H, t, J=6.4 Hz), 3.00 (2H, t, J=6.6 Hz), 3.69 (3H, s), 3.98 (4H, s), 5.67 (1H, s); MS m/z (relative intensity) 212 (M+, 100), 197 (25), 180 (44), 153 (73).

4-Monoethylene ketal-cyclohexylidene ethanol (9).

To a solution of the ester 8 (2.9 g, 13.7 mmol) in anhydrous toluene (100 mL) at −78° C. under Argon was added dropwise in 1.5 h diisobutylaluminum hydride (1.5M in toluene, 60 mL, 90 mmol). After the addition stirring was continued for 30 min at −78° C. then the reaction was allowed to warm to −50° C. during 1 h. The mixture was quenched by the addition of 2N potassium sodium tatrate, the organic phase was separated, and the aqueous phase extracted with ethyl acetate and ether. The combined organic phases were washed with water and brine and dried ($MgSO_4$), filtered and evaporated. The oily residue was purified by fast filtration through a silica gel column, using ethyl acetate in hexane (55:45) as eluent, to give pure alcohol 9 (1.80 g, 72%) $^1$H NMR ($CDCl_3$, 500 MHz) δ1.698 (4H, m), 2.28 (2H, t, J=6.4 Hz), 2.34 (2H, t, J=6.4 Hz), 3.97 (4H, s), 4.16 (2H d, J=6.8 Hz), 5.44 (1H, t, J=6.8 Hz); MS m/z (relative intensity) 184 (M+, 14), 166 (7), 153 (11), 87 (100).

4-Monoethylene ketal-cyclohexylidene-ethyl diphenylphosphine Oxide (2b).

Allylalcohol 9 (1.66 g, 9 mmol) was dissolved in anhydrous THF (80.0 mL) cooled to 0° C. and n-BuLi (1.6M in hexanes, 5.6 mL, 9 mmol) added under argon with stirring. Recrystallized dry tosylchloride (1.72 g, 9 mmol) was dissolved in anhydrous THF (16 mL) and added to the allylalcohol-BuLi solution under argon at 0° C. The solution was stirred at 0° C. for 5 min and set aside at 0° C. In another dry flask with air replaced by argon n-BuLi (1.6M in hexanes, 11.2 mL, 18 mmol) was added to diphenyl-phosphine (3.1 mL 18 mmol) in anhydrous THF 25 mL) at 0° C. with stirring. The red solution was syphoned under argon pressure at 0° C. to the tetrahydrofuran solution of the allylic rosylate until the orange color persisted. (approximately ½ of the solution was added). The resulting mixture was stirred an additional 30 min at 0° C. and quenched by the addition of water (1 mL). Solvents were evaporated under reduced pressure and the residue was dissolved in dichloromethane (80 mL) and stirred with 10% hydrogen peroxide (40 mL) at 0° C. for 1 h. The dichloromethane layer was separated and washed with cold aqueous sodium sulfite, water and brine, dried (MgSO$_4$) filtered and evaporated. The semi crystalline residue was purified by fast filtration through a silica gel column, (5 cm diameter) using ethyl acetate: benzene: 2-propanol (90:5:5) to give the crystalline phosphine oxide 2b (2.55 g, 77%): $^1$HNMR (CDCl$_3$, 500 MHz) δ1.33 (2H, t, J=6.4 Hz), 1.56 (2H, t, J=6.3 Hz), 2.07 (2H, m), 2.20 (2H, m), 3.11 (2H, m), 3.91 (4H, s), 5.30 (1H, q, J=7.0 Hz), 7.46 (4H, m), 7.52 (2H, m), 7.73 (4H, m); MS m/z (relative intensity) 368 (M+, 80), 323 (40), 230 (51), 202 (100), 166 (89).

19-Nor-3-desoxy-2-ethylene ketal-22-acetoxyhomopregnacalciferol (3b).

Phosphine oxide 2b (66 mg, 180 μmol) was dissolved in anhydrous THF (4 mL), cooled to 0° C. and n-BuLi (1.6M in hexanes, 112 μL, 179 μmol) added under argon with stirring. The solution turned deep orange. The mixture was cooled to −78° C. and the 22-acetoxy-Grundmann ketone 1 (45 mg, 178 μmol) added in anhydrous THF (0.5 mL+1.0 mL). The mixture was stirred under argon at −78° C. for 1 h (at that time the solution became colorless) and at rt for 18 h. Ethyl acetate was added and the organic phase washed with water, brine, dried (anh. MgSO$_4$), filtered and evaporated. The residue was dissolved in 20% ethyl acetate in hexane, passed through a silica Sep-Pak and washed with 40 mL of the same to give the 19-nor-homopregnacalciferol derivative 3b. The Sep-Pak was then washed with 20% 2-propanol in hexane to recover some unchanged diphenylphosphine oxide. Compound 3b was purified by HPLC (10% ethyl acetate in hexane, Zorbax Sil 9.4×25 cm) to give the 19-nor-homopregnacalciferol derivative 3b (20 mg, 28%). $^1$H NMR (CDCl$_3$, 500 MHz) δ: 0.583 (3H, 2, 18-CH$_3$), 1.025 (3H, d, J=7.0 Hz, 21-CH$_3$), 2.06 (3H, s, OCOCH$_3$), 2.82 (1H, m, 9β-H), 3.80 (1H, dd, J=10.9, 7.7 Hz, one of 22-H), 3.97 (4H, s, —O—CH$_2$—), 4.09 (1H, dd, J=10.9 Hz, 3.0 Hz, one of 22-H), 5.82 (1H, d, J=11.1 Hz, 7-H), 6.12 (1H, d, J=11.1 Hz, 6-H), exact mass calcd for C$_{25}$H$_{38}$O$_4$ 402.2770, found 402.2776. MS m/z (rel. int.), 402 (M+, 23), 342 (6), 206 (12) 175 (11), 133 (11), 99 (22). UV (in EtOH) λ$_{max}$: 243, 251.5, 261 nm 19-Nor-3-desoxy-2-ethylene ketal-22-hydroxyhomopregnacalciferol (4b).

Acetoxy-homopregnacalciferol 3b (19 mg, 50 μmol), was dissolved in 1 mL anh THF cooled to 0° C. and LiAlH$_4$ (25 mg) added under argon with stirring. The mixture was stirred for an additional 30 min. at 0° C. and 25 min at RT. The mixture was cooled to 0° C. and the excess LiAlH$_4$ decomposed by the careful addition of wet ethyl acetate. More ethyl acetate was added, and the organic phase washed with water and brine, dried (anh. MgSO$_4$), filtered and evaporated. The residue was dissolved in 20% ethyl acetate in hexane, passed through a silica Sep-Pak and washed with the same to give the 19-nor-22-hydroxy-homopregnacalciferol derivative 4b. (18.86 mng, quant yield). $^1$H NMR (CDCl$_3$, 500 MHz) δ0.584 (3H, s, 18-CH$_3$), 1.062 (3H, d, J=6.6 Hz, 21-CH$_3$), 2.82 (1H, m, 9β-H), 3.39 (1H, m, one of 22-H$_2$), 3.65 (1H, m, one of 22-H$_2$), 3.97 (4H, s, —O—CH$_2$—), 5.82 (1H, d, J=11.1 Hz, 7-H), 6.12 (1H, d, J-11.1 Hz, 6-H), UV (in EtOH) λ$_{max}$: 243, 251.5, 261 nm. exact mass calcd for C$_{23}$H$_{36}$O$_3$ 360.2664, found 360.2663, MS m/z (rel. int.), 360 (M+, 82), 301 (22), 267 (12), 206 (58)

19-Nor-3-desoxy-2-ethylene ketal-homopregnacalciferol 22-aldehyde (5b).

A solution of oxalyl chloride (30 μL, 0.34 mmol) in anhydrous dichloromethane (0.5 mL) was added dropwise to a stirred solution of dimethyl sulfoxide (40 μL, 0.57 mmol) in 200 μL anhydrous dichloromethane at −60° C. under argon atmosphere. After the mixture was stirred for 10 min at −60° C., the solution of the alcohol 4b (17 mg, 47 μmol) in 500 μL anh dichloromethane was slowly added, and the flask was rinsed with an additional 500 μL anh dichloromethane. The mixture was stirred for 30 min at −60° C., and 500 μL triethylamine was added at −60° C. The mixture was stirred for 5 min, warmed to 0° C. and extracted with ether. The ether phase was washed with brine and dried (anh. MgSO$_4$), filtered and evaporated. The residue was dissolved in 30% ethyl acetate in hexane, passed through a silica Sep-Pak and washed with the same. The crude compound was purified by HPLC (10% ethyl acetate in hexane, Zorbax Sil 9.4×25 cm) to give the 19-nor-homopregnacalciferol 22 aldehyde derivative 5b. (11.53 mg, 68%) $^1$H NMR (CDCl$_3$, 500 Mhz) δ: 0.609 (3H, s, 18-CH$_3$), 1.138 (3H, d, J=6.65 Hz, 21-CH$_3$), 2.84 (1H, m, 9β-H), 3.97 (4H, s, O—CH$_2$), 5.83 (1H, d, J=11.1 Hz, 7-H) 6.12 (1H, d, J=11.1 Hz, 6-H), 9.59 (1H, d, J=3.0 Hz, 22-H). MS m/z (re. Int), 358 (M+23), 330 (3), 206 (8), 119 (100), 100 (38). exact mass calcd for C$_{23}$H$_{34}$O$_3$ 358.2508 found 358.2508. UV (in EtOH) λ$_{max}$: 243, 251.5, 261 nm 19-Nor-3-desoxy-2-ethylene ketal-20-oxopregna-calciferol (6b).

A CuAc$_2$-dipyridyl-DABCO (1,4-diazabicyclo(2.2.2)octane) solution in anh DMF was prepared from dipyridyl (12 mg, 0.77 mmol) CuAc$_2$ (12 mg, 0.72 mmol) and DABCO (190 mg, 1.7 mmol) in anhydrous dimethyl formamide (2 mL). The 22-aldehyde 5b (3 mg, 8.4 μmol) was dissolved in anh. dimethyl formamide (0.5 mL) and the above CuAc$_2$-dipyridyl-DABCO DMF solution added (0.4 mL). The mixture was protected from light and air was bubbled into this solution for 22 h at RT with stirring. Water was added and the mixture extracted with ether. The ether phase was washed with brine and dried (anh. MgSO$_4$), filtered and evaporated. The residue was dissolved in 30% ethyl acetate in hexane, passed through a silica Sep-Pak and washed with the same. The crude compound was purified by HPLC (10% ethyl acetate in hexane, Zorbax Sil 9.4×25 cm) to give the 19-nor-20-oxopregnacalciferol derivative 6b (1.8 mg, 60%) $^1$H NMR. (CDCl$_3$, 500 MHz) δ: 0.518 (3H, s, 18-CH$_3$), 2.13 (3H, s, 21-CH$_3$), 2.85, (1H, m, 9β-H), 3.97 (4H, s, O—CH$_2$), 5.84 (1H, d, J=11.2 Hz, 7-H), 6.11 (1H, d, J=11.2 Hz, 6-H). MS m/z (rel. int) 344 (M+,60), 301 (12) 239 (25) 206 (14), 147 (35), 105 (45), 91 (55), 55 (22). exact mass calcd for C$_{22}$H$_{32}$O$_3$ 344.2351 found 344.2366 UV (in EtOH) λ$_{max}$: 243, 251.5, 261 nm.

19-Nor-3-desoxy-2,20-dioxopregnacalciferol (6c).

The 2-ketal-20-oxopregnacalciferol 6b (445 μg) was treated under argon atmosphere with a 80% acetic acid 20% water mixture (100 μL) at 70° C. oil bath temperature for 15 min. The acetic acid-water was removed by purging with nitrogen or by the addition of toluene and evaporating the azxeotropic mixture. The residue was dissolved in 30% ethyl acetate in hexane mixture and purified by HPLC (30% ethyl acetate in hexane, Zorbax Sil 9.4×25 cm) to give the 2,20-dioxopregnacalciferol 6c. (273 μg, 70%). $^1$H NMR. (CDCl$_3$, 500 MHz) δ: 0.526 (3 H, s, 18-CH$_3$), 2.14 (3H; s, CO—CH$_3$), 2.86, (1H, m, 9β-H), 5.83 (1H, d, J=11.2 Hz, 7-H), 6.28 (1H, d, J=11.2 Hz, 6-H). MS m/z (rel. int) 300 (M+, 100), 257 (56), 239 (9), 135 (44). exact mass calcd for C$_{22}$H$_{28}$O$_2$ 300.2859 found: 300.2074 UV (in EtOH) λ$_{max}$: 252.5, shoulders at 245 and 260 nm.

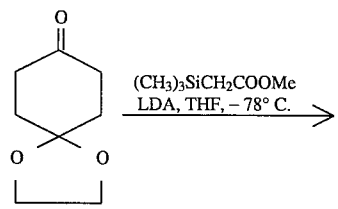
7
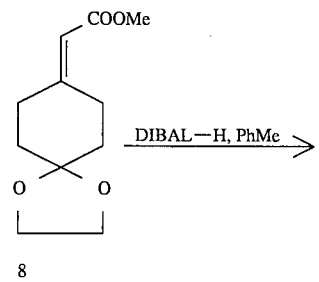
8
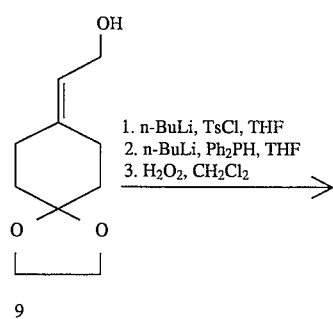
9
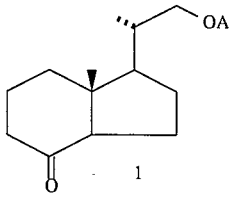
1
+
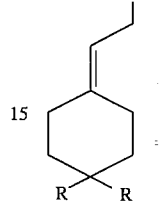
2a  R = H, H
2b  R = −O−CH$_2$ / −O−CH$_2$
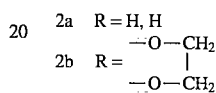
2b
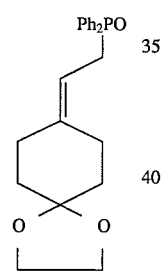
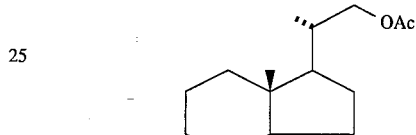
3a  R = H, H
3b  R = −O−CH$_2$ / −O−CH$_2$
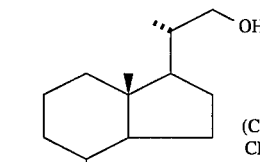
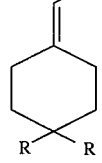
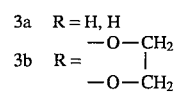
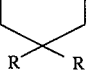
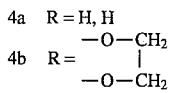
4a  R = H, H
4b  R = −O−CH$_2$ / −O−CH$_2$

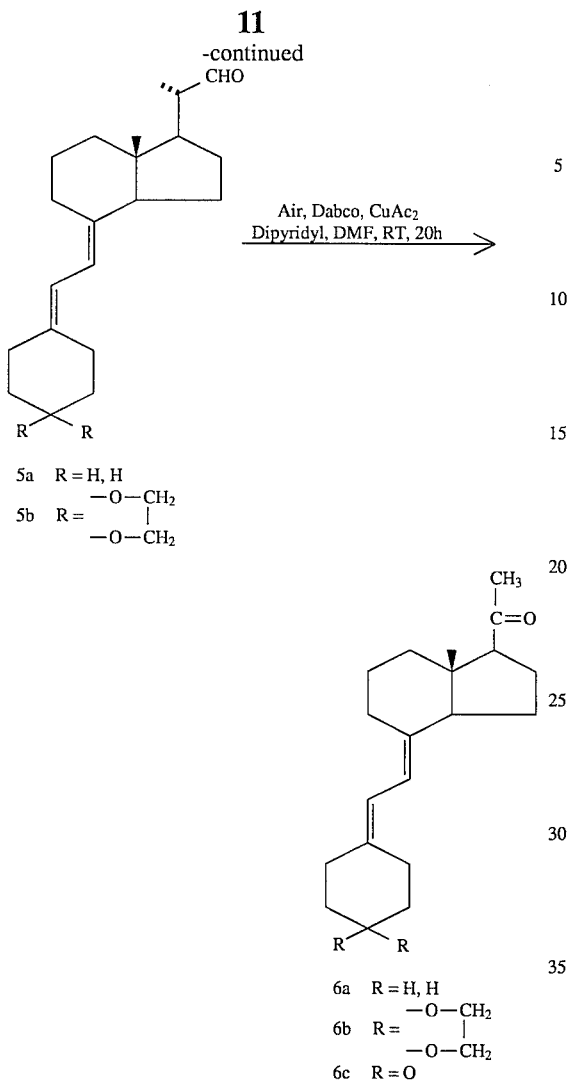

5a  R = H, H
5b  R = −O−CH₂ / −O−CH₂

6a  R = H, H
6b  R = −O−CH₂ / −O−CH₂
6c  R = O

EXAMPLE 3

RECEPTOR BINDING ASSAY OF VITAMIN D ANALOGUES WITH THE PROGESTERONE RECEPTOR

This investigation was carried out to test the ability of vitamin D analogues which share some basic structural features with progesterone to bind the progesterone receptor. This test is part of an effort to identify more potential progesterone antagonists with vitamin D structural backbone.

Experimental Outline

Cell culture and extract preparation: Human Breast Adenocarcinoma cells (MCF-7 cells) extract is used as the progesterone receptor source. The cells were grown to confluency in phenol red-free DMEM with 10% calf serum. After replacing the medium, the cells were dosed with 10 nM Estradiol and incubated for an additional 24 hours to induce the expression of the progesterone receptor. The cells were washed with Hanks Balanced Salt Solution (HBSS: 5.0 mM KCl, 0.3 mM $KH_2PO_4$, 138 mM NaCl, 4.0 mM $NaHCO_3$, 0.3 mM $Na_2HPO_4$, 5.6 mM D-Glucose, 1.3 mM CaCl2 and 0.5 mM MgCl2.6H2O) and then incubated with Ca/Mg-free HBSS+1 mM EDTA for 5–10 minutes at 37° C. After harvesting, the cells were pelleted by centifugation for 5.0 minutes at 4.0° C. The cell pellet was then resuspended in TDG buffer (10 mM Tris-HCl, pH 7.4, 0.5 mM DTT and 50% Glycerol) and sonicated for 15 seconds. The cytosolic fraction was obtained by centrifugation at 50,000 RPM for 20 minutes in TLA 100.2 rotor. The supernatent (cytosol) was removed and stored on ice for use in the binding assay. The Cytosolic fraction was always prepared fresh.

Binding Assay: The ability of the test compounds to compete for binding to the progesterone receptor was tested as follows:

1—The incubation mix consisted of the following:
  100 µl 3H-R5020 (20 nM)
  5 µl Ethanol or test compound in the ethanol providing a 400 fold excess of compound
  100 µl MCF-7 Cell Extract 2—The mixture was incubated 12–14 hours on ice.

3—250 µl of 50% HAP slurry was added+3 mL of TDG buffer.

4—The samples are allowed to sit on ice for 30 minutes with vortexing every 10 minutes.

5—The HAP was pelleted by centrifugation at 1500 rpms for 3 minutes.

6—The pellet was washed three more times with TDG buffer.

7—The final pellet was resuspended in 1 ml Ethanol, vortexed and allowed to sit at room temperature for 30 minutes with vortexing every 10 minutes.

8—The samples were finally centrifuged at 2000 rpms. The supernatent was removed, mixed with counting fluid and the amount of radioactivity in each sample was determined by counting in a beta scintillation counter.

Results:

The results of this screening study are in Table 1, and indicate the ability of some of the vitamin D analogues to compete with progesterone for binding to its receptor. The 3-desoxy-20-oxo-19-nor-pregnacalciferol (6a) did bind to the PR but to a significantly lesser degree (40%) than the previously synthesized 20-oxopregnacalciferol. Also, the intermediate 22-alcohol 4a and the 22-aldehyde 5a did also bind to the PR, the latter compound binding 1.5 times more than the 20-ketone 6a.

As shown in the Table 1, 3-desoxy-2,20-dioxo-19-nor-pregnacalciferol (6c) has almost the same binding activity to the PR, as the previously examined 20-oxopregnacalciferol, whereas the intermediate 22-alcohol 4b, and the 22-aldehyde 5b and the mono-protected 2,20-dione 6b did also bind to the PR but to a lesser degree.

TABLE 1

Competitive Binding of the 3-Desoxy-20-oxo-19-nor-pregnacalciferol, its 2-oxo Analog, and Intermediate Compounds to the Progesterone Receptor.

| Test Compound | Total Binding (DPM) ± S.D. | % Inhibition |
|---|---|---|
| ³H-R5020 | 4758 ± 145 | — |
| +R5020 | 750 ± 231 | 84 |
| +20-oxopregnacalciferol | 1950 ± 170 | 59 |
| +4a | 4139 ± 62 | 13 |
| +5a | 3045 ± 90 | 36 |
| +6a | 3616 ± 171 | 24 |
| +4b | 2881 ± 152 | 40 |
| +5b | 2546 ± 120 | 47 |
| +6b | 2531 ± 165 | 47 |
| +6c | 2036 ± 133 | 58 |

Experimental Notes:

1—The source of the progesterone receptor is the cytosolic fraction of MCF-7 cells (human breast cancer cell line) which were dosed with Estradiol 24 hours prior to harvesting and processing.
2—The cytosolic fractions used in all the binding measurements were freshly prepared. No frozen extracts were used.
3—All competitive compounds were added at 400× fold excess of the labelled R5020. The final ethanol concentration did not exceed 5% of the total volume of the incubation mixture.

For treatment purposes, the novel compounds of this invention can be formulated as solutions in innocuous solvents, or as emulsions, suspensions or dispersions in suitable innocuous solvents or carriers, or as pills, tablets or capsules, containing solid carriers according to conventional methods known in the art. For topical applications the compounds are advantageously formulated as creams, ointments or similar vehicles suitable for transdermal topical applications. Any such formulations may also contain other pharmaceutically acceptable and non-toxic excipients such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal, or topically in the form of suitable transdermal patches. For birth control purposes, the compounds of this invention are administered to subjects in dosages sufficient to bind to the progesterone receptor (PR) so as to block the binding of progesterone to the PR thus resulting in the prevention of pregnancy or in an abortion. Suitable dosage amounts are from 0.1 to 20 mg/kg of compound per day, such dosages being adjusted, depending on the response or condition of the subject as is well-understood in the art.

We claim:

1. A compound having the formula

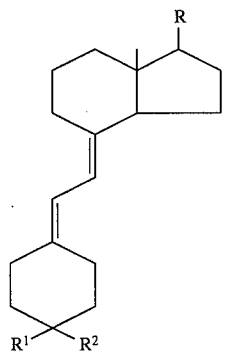

where $R^1$ and $R^2$ each represent hydrogen or taken together $R^1$ and $R^2$ represent an oxo group or a ketal group —O—$(CH_2)_n$—O— where n is an integer from 2 to 5, and where R represents —$COCH_3$, —$CHCH_3CHO$, or —$CHCH_3CH_2OH$.

2. 3-desoxy-20-oxo-19-nor-pregnacalciferol.
3. 3-desoxy-22-hydroxy-19-nor-homopregnacalciferol.
4. 3-desoxy-22-aldehyde-19-nor-homopregnacalciferol.
5. 3-desoxy-2,20-dioxo-19-nor-pregnacalciferol.
6. 3-desoxy-2-ethylene ketal-22-hydroxy-19-nor-homopregnacalciferol.
7. 3-desoxy-2-ethylene ketal-22-aldehyde-19-nor-homopregnacalciferol.
8. 3-desoxy-2-ethylene ketal-20-oxo-19-nor-pregnacalciferol.
9. A birth control method for a female mammal which comprises administering to the mammal an amount of a vitamin D compound sufficient to block binding of progesterone to the progesterone receptor in said mammal, said vitamin D compound is selected from a compound having the formula

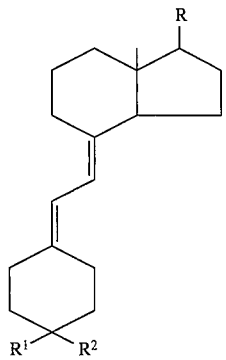

where $R^1$ and $R^2$ each represent hydrogen or taken together $R^1$ and $R^2$ represent an oxo group or a ketal group —O—$(CH_2)_n$—O— where n is an integer from 2 to 5, and where R represents —$COCH_3$, —$CHCH_3CHO$, or —$CHCH_3CH_2OH$.

10. The method of claim 9 wherein said vitamin D compound is administered in an amount of from about 0.1 mg/kg to about 20 mg/kg per day depending upon the vitamin D compound administered.

11. The method of claim 9 wherein said vitamin D compound is administered daily to said mammal for about 3 days to about 1 month.

12. The method of claim 9 wherein said vitamin D compound is administered orally in a liquid vehicle ingestible by and non-toxic to said mammal.

13. The method of claim 9 wherein said vitamin D compound is combined with a non-toxic pharmaceutically acceptable carrier prior to administration.

14. The method of claim 9 wherein said vitamin D compound used is 3-desoxy-20-oxo-19-nor-pregnacalciferol.

15. The method of claim 9 wherein said vitamin D compound used is 3-desoxy-22-hydroxy-19-nor-homopregnacalciferol.

16. The method of claim 9 wherein said vitamin D compound used is 3-desoxy-22-aldehyde-19-nor-homopregnacalciferol.

17. The method of claim 9 wherein said vitamin D compount used is 3-desoxy-2,20-dioxo-19-nor-pregnacalciferol.

18. The method of claim 9 wherein said vitamin D compound used is 3-desoxy-2-ethylene ketal-22-hydroxy-19-nor-homopregnacalciferol.

19. The method of claim 9 wherein said vitamin D compound used is 3-desoxy-2-ethylene ketal-22-aldehyde-19-nor-homopregnacalciferol.

20. The method of claim 9 wherein said vitamin D compound used is 3-desoxy-2-ethylene ketal-20-oxo-19-nor-pregnacalciferol.

21. The method of claim 9 wherein said vitamin D compound is administered to women prior to the onset of a pregnancy.

22. The method of claim 9 wherein said vitamin D compound is administered to women subsequent to the onset of a pregnancy.

23. The method of claim 9 wherein the vitamin D compound is administered in a slow release formulation.

24. The method of claim 9 wherein the vitamin D compound is administered daily in divided dosages.

* * * * *

UNITED STATES PATENT AND TRADEMARK OFFICE
CERTIFICATE OF CORRECTION

PATENT NO. : 5,614,512
DATED : March 25, 1997
INVENTOR(S) : Hector F. DeLuca et al It is certified that error appears in the above-indentified patent and that said Letters Patent is hereby corrected as shown below:

Please add the following paragraph to col. 1 of the specification after the title but before the first paragraph:

---This invention was made with United States Government support awarded by the National Institutes of Health (NIH), Grant #DK-14881. The United States Government has certain rights in this invention.---

IN THE CLAIMS:

Claim No. 17, col. 14, line 46    Delete the word "compount" and substitute therefor ---compound---

Signed and Sealed this

Seventh Day of October, 1997

Attest:

BRUCE LEHMAN

*Attesting Officer*    *Commissioner of Patents and Trademarks*